United States Patent

Broderick

[11] Patent Number: 5,813,971
[45] Date of Patent: Sep. 29, 1998

[54] MAGNOTHERAPY DEVICE

[75] Inventor: Nigel Broderick, Saltash, United Kingdom

[73] Assignee: Ecoflow Limited, United Kingdom

[21] Appl. No.: 744,969

[22] Filed: Nov. 7, 1996

[30] Foreign Application Priority Data

Nov. 17, 1995 [GB] United Kingdom .................. 9523513

[51] Int. Cl.$^6$ ........................................ A61N 1/00
[52] U.S. Cl. ................................................ 600/15
[58] Field of Search ........................................ 600/9–15

[56] References Cited

U.S. PATENT DOCUMENTS

| 5,085,626 | 2/1992 | Frey ........................... 600/15 |
| 5,226,020 | 7/1993 | Li et al. ....................... 600/9 |
| 5,304,111 | 4/1994 | Mitsuno et al. ............. 600/15 |
| 5,514,072 | 5/1996 | Ardizzone ................... 600/15 |

FOREIGN PATENT DOCUMENTS 2255722  11/1992  United Kingdom ............ 600/15

*Primary Examiner*—John P. Lacyk
*Attorney, Agent, or Firm*—Ira S. Dorman

[57] ABSTRACT

A housing comprising mutually engageable top and bottom parts 4 and 5 which contain a lightweight ceramic plate magnet 6 capable of producing a high field strength. A keeper plate 7 is placed on top of the magnet overhanging its longitudinal edges so that blood flowing beneath the device successively encounters alternating north-south-north magnetic poles. The housing is secured to the body by a strap 2 which is held between opposed lands 20, 31 and 19, 32.

10 Claims, 3 Drawing Sheets

MAGNOTHERAPY DEVICE

TECHNICAL FIELD OF THE INVENTION

This invention relates to a device for use in magnotherapy as practised on the human or animal body.

BACKGROUND

Magnotherapy is a therapeutic process which is sometimes performed by physiotherapists using a pulsed magnetic field to alleviate certain diseases and generally improve the health of the recipient. However, the equipment used is large and extremely expensive and would not be practical for use on a personal basis.

The present invention seeks to provide a device for use in magnotherapy which is patentably different from known devices.

SUMMARY OF THE INVENTION

The present invention proposes a magnotherapy device comprising a housing provided with means for securing the housing onto the body with a contact surface of the housing positioned against the body, the housing containing magnetic field-producing means arranged to successively present opposite magnetic poles to blood flowing in a direction which is substantially parallel to said contact surface.

The arrangement of the magnetic means ensures that blood flowing beneath the housing, in the field of the magnets, will pass through changes in the polarity of the magnetic field, thereby simulating the pulsed magnetic fields produced by known magnotherapy equipment.

The magnetic field-producing means preferably produces a magnetic field strength of at least 150 gauss at a distance of 10 mm from the housing, and preferably at least 250 gauss at said distance. Ceramic magnets are preferred since they are capable of producing the required strength without being unacceptably large or heavy.

The housing may be moulded of plastics or formed from a non-ferrous metal.

BRIEF DESCRIPTION OF THE DRAWINGS

The following description and the accompanying drawings referred to therein are included by way of non-limiting example in order to illustrate how the invention may be put into practice. In the drawings.

DETAILED DESCRIPTION OF THE DRAWINGS

Figure 1:
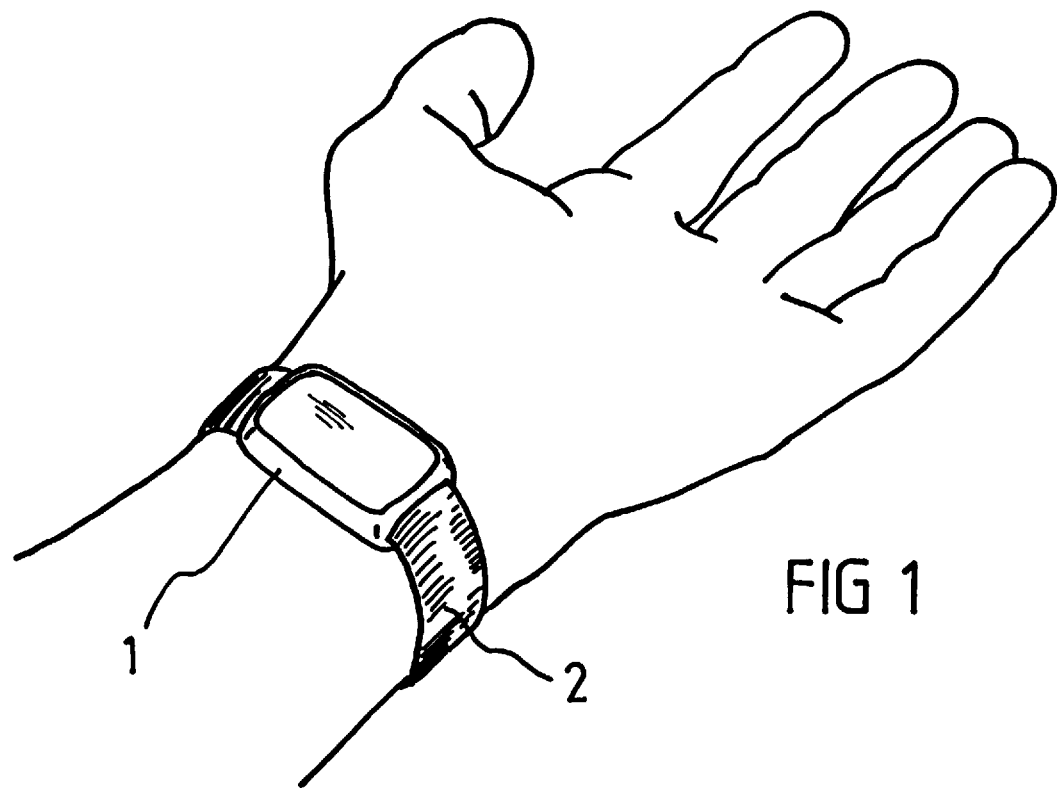
FIG. 1 is a general view of a first form of magnotherapy device of the invention.
Figure 6:
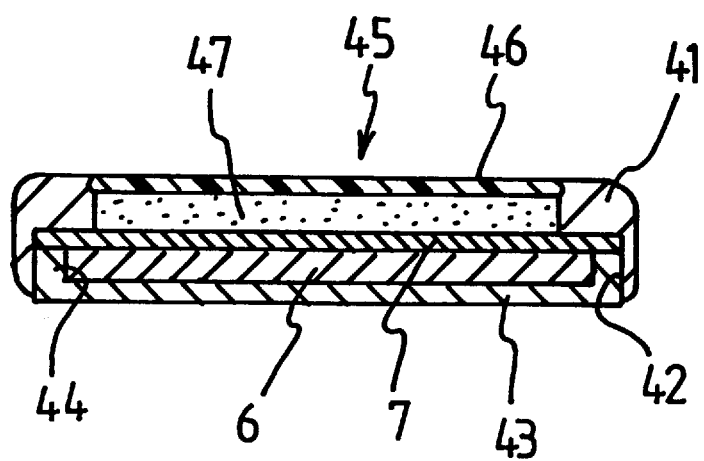
FIG. 6 is a transverse section through a second form of the device.

Referring to FIG. 1, the magnotherapy device comprises a housing 1 which is secured to an elasticated wrist band 2 to enable the device to be conveniently worn on the wrist.

Figure 2:
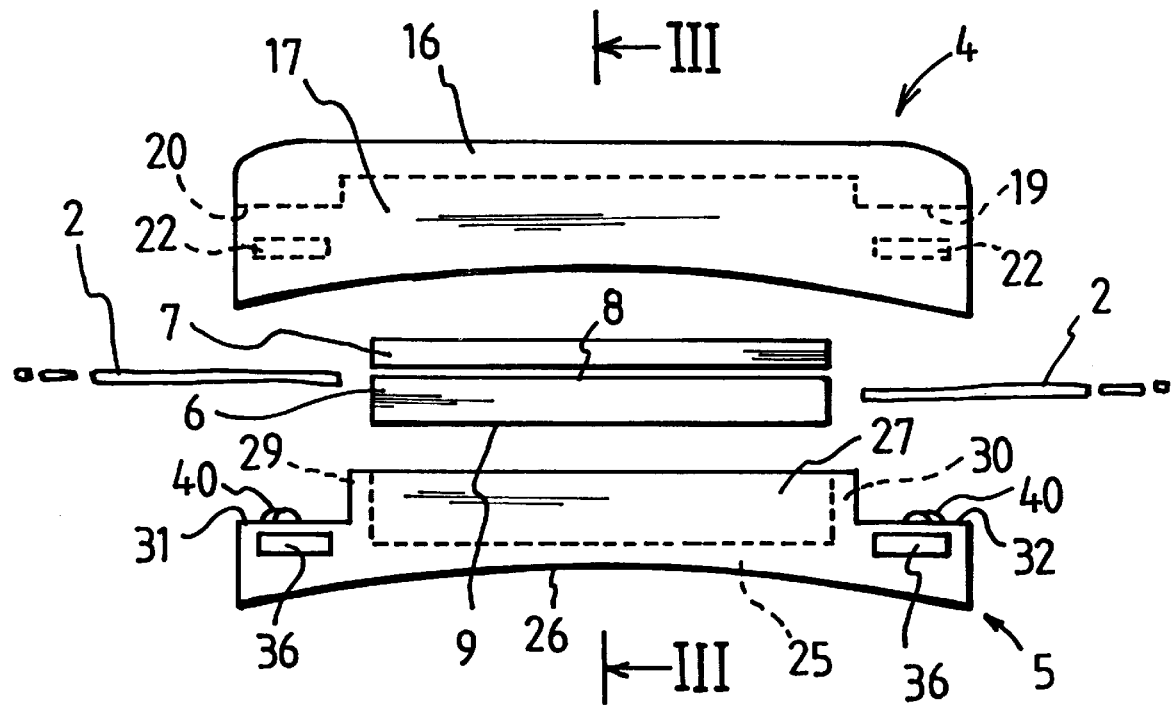
FIG. 2 is an exploded side elevation of the device.
Figure 3:
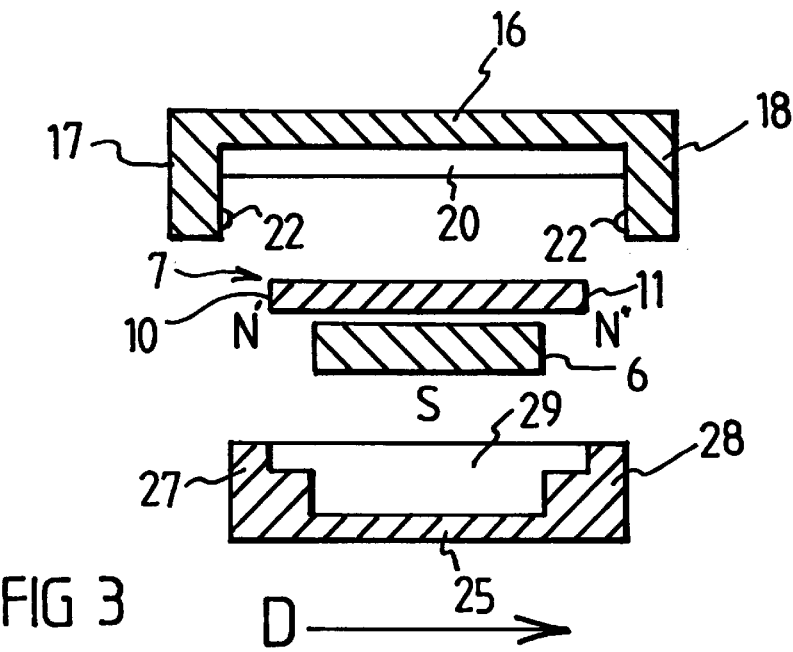
FIG. 3 is transverse section III—III of FIG. 2.

Referring to FIGS. 2 and 3, the housing 1 is moulded of plastics and comprises a top part 4 and a bottom part 5, which will be described in more detail below. The housing contains a ceramic plate magnet 6 and a keeper plate 7. The north and south magnetic poles of the magnet 6 are disposed on its mutually closest pair of opposed faces 8 and 9. The keeper 7 is held in contact with the top north face 8 and overhangs the magnet 6 along its longitudinal side edges 10 and 11 (FIG. 3) so that the magnetic field is concentrated in the keeper effectively producing a pair of secondary north poles N' and N" on opposite sides of the south pole S. Thus, as blood flows through the veins of the wrist in a direction D, transversely of the housing, the blood passes through alternate north, south and north poles of the magnetic field. A suitable magnet 6 produces a magnetic field strength of about 620 gauss at a distance of 5 mm from the magnet and about 280 gauss at a distance of 10 mm.

Figure 4:
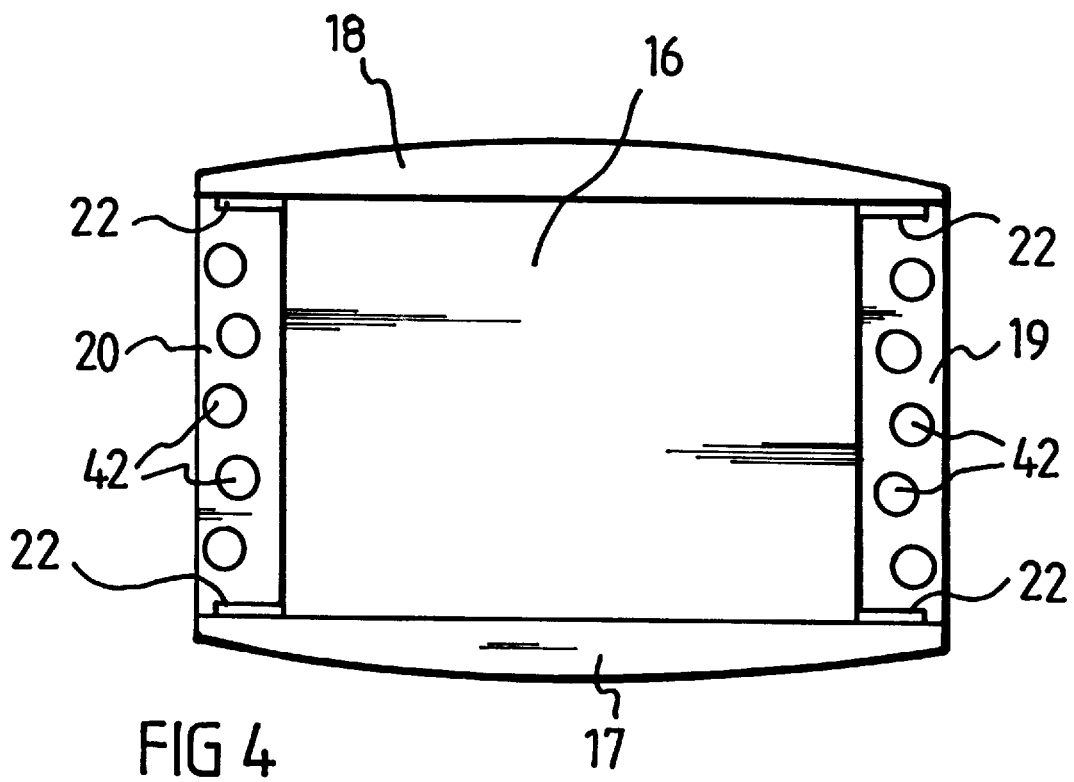
FIG. 4 is a bottom plan elevation of the top part shown in FIGS. 2 and 3.

In more detail, the top part 4 comprises a top wall 16 of substantially plano-rectangular shape (FIGS. 2–4). Two side walls 17 and 18 depend from the longitudinal edges of the top wall 16, and these are bridged at each end by shallow transversely extending platforms 19 and 20. The side walls are each provided with a pair of longitudinally extending ribs 22 immediately below the platforms 19 and 20.

The bottom part 5 is configured to be received between the side walls 17 and 18 and comprises a bottom wall 25, the underside 26 of which is slightly concave in the longitudinal direction to fit comfortably in contact with the skin of the wrist. (It may also be concave in the transverse direction if desired.) The longitudinal edges of the bottom wall 25 are provided with upstanding side walls 27 and 28, the inner faces of which are stepped outwardly to receive and locate the magnet 6 and, positioned on said steps, the keeper 7. The magnet and keeper are longitudinally located by end walls 29 and 30 which stand above lands 31 and 32 formed at each end of the bottom wall 25.

The top part 4 can be snap-engaged with the bottom part 5, containing the magnet and keeper 6, 7, by engagement of the ribs 22 in corresponding recesses 36 in the opposed side faces of the bottom part. (It will be appreciated that the bottom part could be provided with ribs which snap-engage with recesses in the top part.) When the two parts 4 and 5 are thus connected the lands of the platforms 19, 20 are directly opposed to the lands 31 and 32, but are mutually spaced sufficient to receive and grip opposite ends of the band 2. The engagement of the lands with the band 2 may be further enhanced by projections 40 on lands 31 and 32 which deform or pierce the band to enter corresponding recesses 42 in the opposed lands 19 and 20.

A non-elasticated wrist band can be used. In this case the middle region of the band is passed through the housing, secured between the keeper 7 and the top wall 16. The free ends of the band are provided with mutually engageable clasp fasteners, at least one of which can be adjusted in position along the band. An advantage of this kind of band is that it can be extended by insertion of a second length provided with similar clasp fasteners to engage the fasteners of the first band. Such an enlarged band could, for example, be used to secure the device to the thigh with the magnets overlying the femoral artery or other major blood vessel, or to secure the device about the body of an animal. The device could in fact be attached to any part of the human or animal body having a sufficient blood flow near the surface of the skin. The device may also be secured using an adhesive plaster for example.

Figure 5:
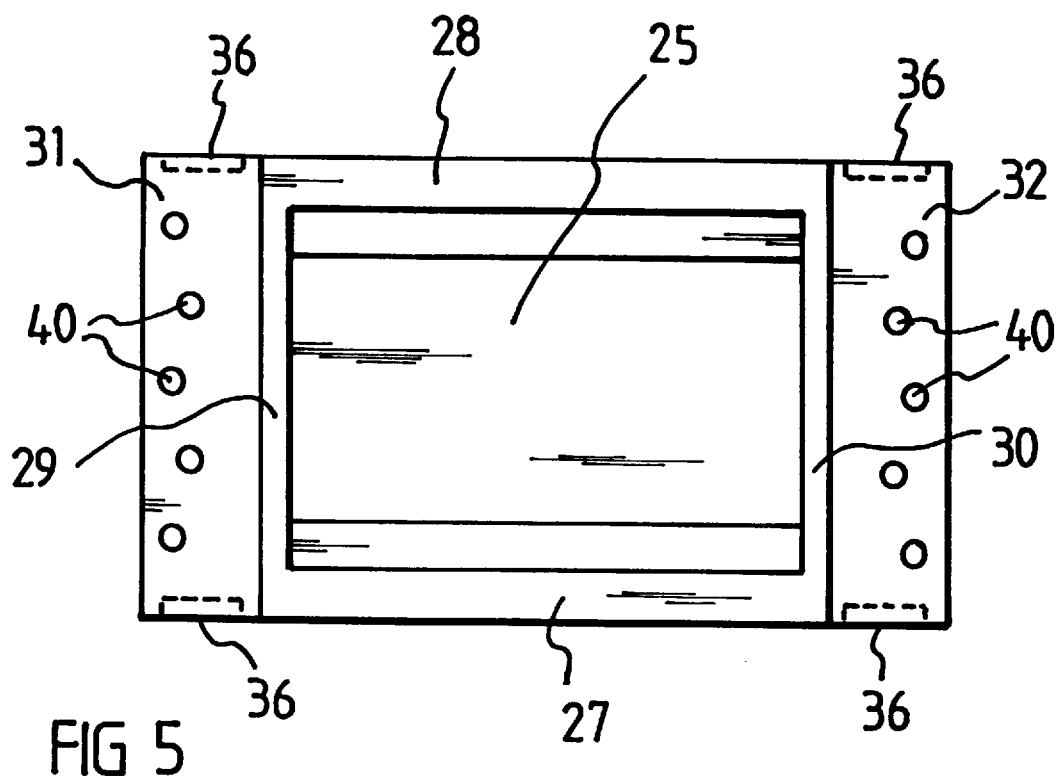
FIG. 5 is a top plan elevation of the bottom part shown in FIGS. 2 and 3.

The device shown in sectional detail in FIG. 5 again contains a magnet 6 and keeper 7 as described above, but in this instance they are mounted in a plano-rectangular housing 41 cast of an alloy. The housing may be painted or gold plated. The magnet and keeper are bonded together by an adhesive and then inserted in a rectangular recess 42 in the bottom of the housing. A back plate 43 with inturned edges 44 is pressed into the recess 42 to hold the magnet and keeper in place. The top wall of the housing has a window opening 45 containing a glass plate 46, and the space between the keeper 7 and the plate 46 is filled with silicone rubber sealant 47 or similar filler. The opposed ends of the housing may be provided with a pair of spring-loaded alloy clasps (not shown) for securing the device onto the wrist.

The way in which magnotherapy works is not fully understood. It is known however that the blood transports essential substances such as oxygen and enzymes to the cells and tissues of the body and carries away waste products. For example, oxygen is carried by haemoglobin in the red blood cells, which contains iron, and carbon dioxide is carried in the blood plasma as bicarbonate. It is believed that after passing through the magnetic field produced by the device of the invention, certain important components of the blood are ionised by magnetic induction and the ability of the blood to carry components such as oxygen, nutrients and waste products is significantly improved. This is equivalent to improving the circulation, and results in accelerated healing, pain reduction, and a general improvement in the condition of the body tissues.

Whilst the above description lays emphasis on those areas which, in combination, are believed to be new, protection is claimed for any inventive combination of the features disclosed herein.

I claim:

1. A magnotherapy device comprising:
   a housing of substantially plano-rectangular configuration having a contact surface adapted for positioning against a human or animal body, said housing comprising a top part and a bottom part, said top part comprising a substantially rectangular top wall having a pair of opposed end edges and a longer pair of opposed side edges, and two side walls depending from said pair of opposed side edges, said bottom part comprising a bottom wall and four side walls upstanding from said bottom wall, said side walls of said bottom being adapted to be received between said side walls of said top part, and said side walls and said bottom wall of said bottom part defining a well;
   means for securing the housing to said human or animal body; and
   magnetic field-producing means received in said well defined in said bottom part of said housing and arranged to successively present opposite magnetic poles to blood flowing through said human or animal body in a direction which is substantially parallel to said contact surface, said magnetic field-producing means producing a magnetic field strength of at least 150 gauss at a distance of 10 mm from said housing, and comprising a ferrous metal keeper plate and a plate magnet having opposite faces bounded by opposite edges, said opposite edges being disposed adjacent to said side walls of said bottom part, said plate magnet having first and second magnetic poles at said opposite faces thereof, said first magnetic pole being disposed adjacent to said contact surface and said second magnetic pole being disposed adjacent to said ferrous metal keeper plate, said keeper plate extending substantially beyond said opposite edges of said plate magnet at said second face so as to produce said opposite magnetic pole effect at said contact surface.

2. A magnotherapy device according to claim 1, in which the magnetic field-producing means is arranged to successively present at least three alternating magnetic poles (N-S-N or S-N-S) in said direction of blood flow.

3. A magnotherapy device according to claim 1, in which said magnetic field-producing means produces a magnetic field strength of at least 250 gauss at a distance of 10 mm from the housing.

4. A magnotherapy device according to claim 1, in which said magnetic field-producing means comprises a ceramic magnet.

5. A magnotherapy device according to claim 1, in which said top part comprises a pair of lands disposed adjacent to said opposed end edges, and said bottom part comprises a pair of lands which are opposed to said lands of the top part, and said means for securing the housing to said human or animal body comprises a band which is received between said lands.

6. A magnotherapy device according to claim 5, in which each pair of opposed lands comprises opposed projections and recesses.

7. A magnotherapy device according to claim 5, in which the lands of the top part form platforms which project downwardly from the top wall and extend between the side walls of the top part.

8. A magnotherapy device according to claim 1, in which the two parts of the housing are provided with complementary formations which allow the said parts to be joined by a snap-engagement.

9. A magnotherapy device according to claim 1, in which said contact surface is generally concave.

10. A magnotherapy device according to claim 1, in which said housing is formed in one piece and the magnetic field-producing means is secured in a recess in said housing.

\* \* \* \* \*